United States Patent
Cali et al.

(10) Patent No.: US 9,713,699 B2
(45) Date of Patent: Jul. 25, 2017

(54) TRANSPORT AND STORAGE APPARATUS FOR WOUND CARE EXUDATE

(71) Applicant: NEOGENIX, LLC, Ft. Lauderdale, FL (US)

(72) Inventors: Lawrence J. Cali, East Falmouth, MA (US); Srinivasan Sarangapani, Walpole, MA (US)

(73) Assignee: NEOGENIX, LLC, Fort Lauderdale, FL (US)

( * ) Notice: Subject to any disclaimer, the term of this patent is extended or adjusted under 35 U.S.C. 154(b) by 0 days.

(21) Appl. No.: 14/757,362

(22) Filed: Dec. 22, 2015

(65) Prior Publication Data
US 2016/0263359 A1    Sep. 15, 2016

Related U.S. Application Data

(60) Provisional application No. 62/095,750, filed on Dec. 22, 2014.

(51) Int. Cl.
*A61M 27/00*  (2006.01)
*A61M 1/00*   (2006.01)
*A61M 16/08*  (2006.01)

(52) U.S. Cl.
CPC .......... *A61M 27/00* (2013.01); *A61M 1/0001* (2013.01); *A61M 1/0086* (2014.02);
(Continued)

(58) Field of Classification Search
CPC .............. A61M 1/0086; A61M 1/0088; A61M 1/00023; A61M 2025/0004; A61M 25/0028; A61M 16/0808
See application file for complete search history.

(56) References Cited

U.S. PATENT DOCUMENTS 550,238 A    11/1895  Allen, Jr.
3,394,705 A   7/1968  Abramson
(Continued)

OTHER PUBLICATIONS

Apollo Medical Extrusion on Behance, 15 pages [retrieved on Aug. 2, 2016]. Retrieved from the Internet: <URL: www.behance.net/gallery/14594861/Apollo-Medical-Extrusion.
(Continued)

*Primary Examiner* — Leslie Deak
*Assistant Examiner* — Kai Weng
(74) *Attorney, Agent, or Firm* — Law Office of Arthur M. Antonelli, PLLC (57) ABSTRACT

A device for transporting waste gases and liquid exudates from a wound. The device may include a multi lumen tubing and a connector for securing the multi lumen tubing to a fitting. The multi lumen tubing may include a double wall containment structure with a first lumen and a second lumen. The connector may include a body with a first cavity on one side, a second cavity on another side, and an interior wall located between the first cavity and the second cavity. The interior wall may form a projection in the second cavity. The projection may include an outer surface and a ledge adjacent the outer surface. The projection may cooperate with the multi lumen tubing to form a liquid-gas separator. The ledge may include a bore extending between the first cavity and the second cavity. The bore may house a gas permeable and a liquid impermeable barrier.

18 Claims, 6 Drawing Sheets

(52) U.S. Cl.
CPC ...... *A61M 1/0088* (2013.01); *A61M 16/0808* (2013.01); *A61M 2205/02* (2013.01); *A61M 2205/3344* (2013.01); *A61M 2205/7536* (2013.01)

(56) References Cited

U.S. PATENT DOCUMENTS

| | | | |
|---|---|---|---|
| 3,448,739 A | | 6/1969 | Stark et al. |
| 4,950,224 A | * | 8/1990 | Gorsuch ............ A61B 5/14528 604/6.04 |
| 5,636,643 A | | 6/1997 | Argenta et al. |
| 5,645,081 A | | 7/1997 | Argenta et al. |
| 5,779,649 A | * | 7/1998 | Herbert ............... A61M 1/0056 600/571 |
| 7,615,036 B2 | | 11/2009 | Joshi et al. |
| 7,779,625 B2 | | 8/2010 | Joshi et al. |
| 8,282,611 B2 | | 10/2012 | Weston |
| 8,679,081 B2 | | 3/2014 | Heagle et al. |

OTHER PUBLICATIONS

Custom Multi Lumen Tubing—Multi Lumen Extrusion, 2 page [retrieved on Aug. 2, 2016]. Retrieved from the Internet: <URL: www.pexco.com/markets/medical/multilumen-tubing/#3.

Stock & Custom Medical Tubing & Medical Extrusions, 2 pages [retrieved on Aug. 2, 2016]. Retrieved from the Internet: <URL: www.dukeextrusion.com/.

* cited by examiner

TRANSPORT AND STORAGE APPARATUS FOR WOUND CARE EXUDATE

CROSS REFERENCE TO RELATED APPLICATIONS

This application claims the benefit of U.S. Provisional Application No. 62/095,750 filed on Dec. 22, 2014, which is incorporated by reference herein in its entirety.

FIELD OF THE INVENTION

The present invention generally relates to wound care. More particularly, this invention relates to transport and storage devices for waste gases and exudates related to wound care such as, negative pressure wound therapy and other treatments, including continuous topical oxygen therapy.

BACKGROUND

Negative Pressure Wound Therapy (NPWT) may be used to treat wounds, including acute wounds, chronic wounds, pressure ulcers, and diabetic foot ulcers. For example, a dressing may be applied to a chronic wound to form an airtight seal, and a pump may be connected via a tube to the dressing to evacuate air from the dressing and draw drainage from the wound. NPWT may accelerate wound healing by various mechanisms including: removal of exudate, reduction of edema, contraction of wound edges, stimulation of angiogenesis, changes in the wound edges, and production of granulation tissue. Nevertheless, wound treatment with NPWT may provide limited efficacy should the healing process stall or contraindications, such as advancing infection in the wound, develop. Although oxygen delivery therapies may be used to successfully treat wounds, including wounds that have failed NPWT, a need exists for new devices and systems that may improve patient outcomes and expand access to patients with limited mobility or clinical support.

SUMMARY

Hence, the present invention is directed to devices for the collection, transport and storage of exudate wastes from wound care. A device for transporting waste gases and liquid exudates from a wound may include a multi lumen tubing. The multi lumen tubing may comprise a double wall containment structure. The double wall containment structure may include a first wall which forms an outer containment structure for a first lumen, the outer containment structure including a first end portion, a second end portion, and a first longitudinal axis extending from the first end portion to the second end portion. The double wall containment structure further may include a second wall which forms a tube that defines a second lumen, the tube being spaced from the first wall such that the first and second walls are concentrically aligned about the first longitudinal axis, and such that the first wall and the second wall define the first lumen. Additionally, the device may include a connector for securing the multi lumen tubing to a fitting. The connector may comprise a body having a second longitudinal axis such that the body incudes a first end surface with a first cavity extending into the body from the first end surface, the first cavity being bounded radially about the second longitudinal axis by a first cavity side wall. Also, the body may include a second end surface spaced from the first end surface along the second longitudinal axis. The second end surface may include a second cavity extending into the body from the second end surface, the second cavity being bounded radially about the second longitudinal axis by a second cavity side wall. Moreover, the body may include an interior wall located between the first cavity and the second cavity, the interior wall forming a projection in the second cavity. The projection may comprise an outer surface facing the second cavity side wall, and a ledge adjacent the baffle surface. The ledge may include a bore extending between the first cavity and the second cavity. A hydrophobic filter may be positioned in the bore such that the hydrophobic filter forms a gas permeable and a liquid impermeable barrier between the second cavity and the first cavity.

The second cavity and the second cavity side wall may be configured and dimensioned to connect the multi lumen tubing to the connector. The second cavity and the second cavity side wall may be configured and dimensioned to telescopically receive the first wall of the outer containment structure. The outer surface of the projection, the first wall of the double wall containment structure, and the second wall of the double wall containment structure may cooperate to form a passage that fluidly connects the first lumen, the second lumen and the bore extending between the first cavity and the second cavity. The passage that fluidly connects the first lumen, the second lumen, and the bore extending between the first cavity and the second cavity may be configured and dimensioned to form a liquid-gas separator such that a liquid-gas mixture being conveyed from the first lumen to the second lumen changes flow direction abruptly to separate liquid from the liquid-gas mixture.

The ledge may extend into the second lumen. The second lumen may include a blind end. The second lumen may house absorbent material. The absorbent material may include one or more superabsorbent polymers.

The multi lumen tubing may be flexible. The multi lumen tubing may be designed to convey gases under negative pressure. The multi lumen tubing may be designed to convey a waste gas liquid mixture from a wound. The first lumen may have a first cross-section perpendicular to the first longitudinal axis, the first cross-section having annular shape. The second lumen may have a second cross-section perpendicular to the first longitudinal axis, the second cross-section being of different shape than the first cross-section. The second cross-section may be of circular shape.

The hydrophobic filter may include a plug of filter media. The filter media may be a POREX filter media. The body may be configured and dimensioned to mate with a standardized fluid fitting.

DESCRIPTION OF THE DRAWINGS

In the accompanying drawings, which form a part of the specification and are to be read in conjunction therewith and in which like reference numerals (or designations) are used to indicate like parts in the various views.

DESCRIPTION

Figure 1:
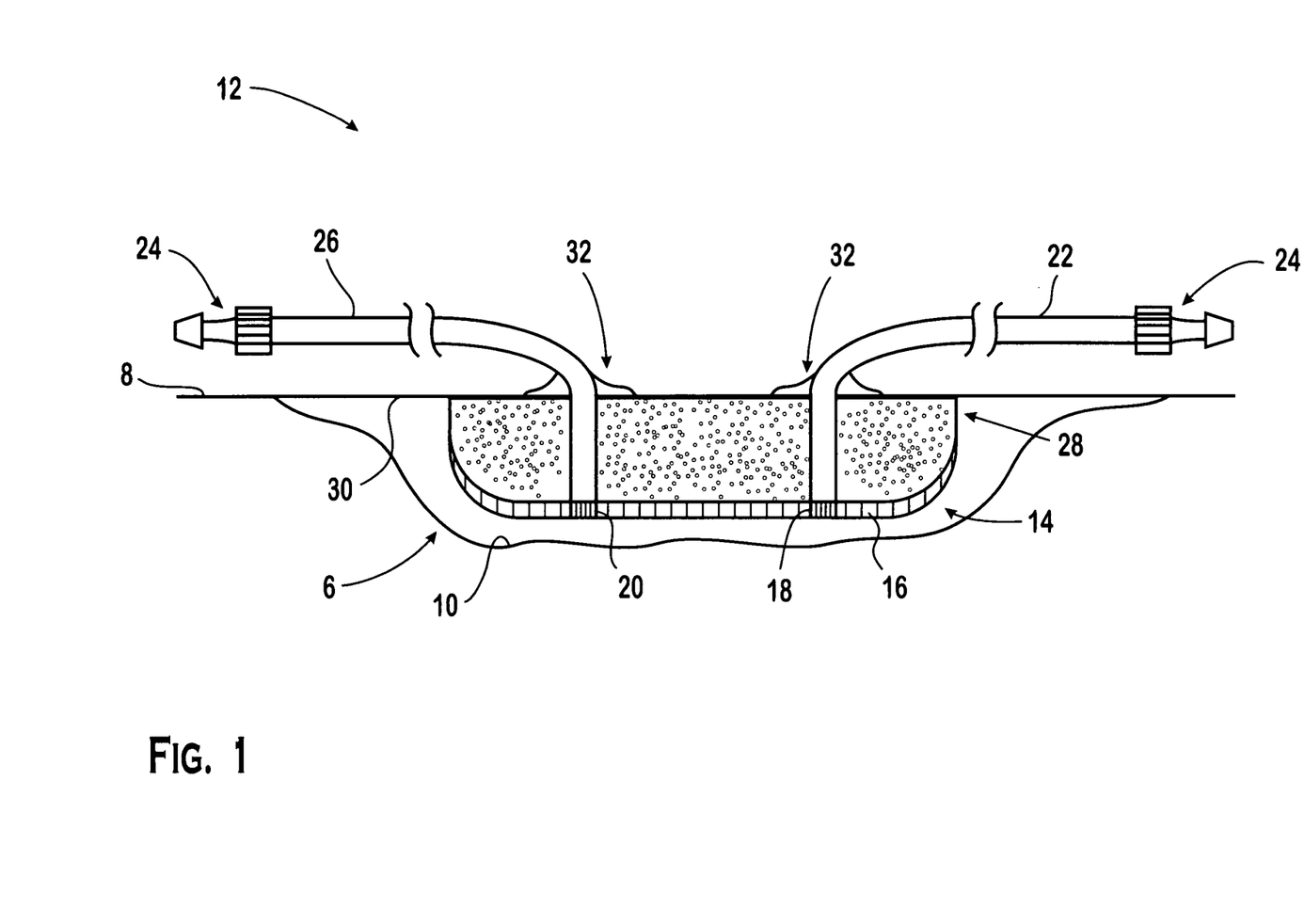
FIG. 1 is a cross-sectional view of an embodiment of a dressing assembly for the application of negative pressure wound therapy, transdermal oxygen delivery, or combinations thereof to a wound.

FIG. 1 shows an illustrative wound cavity 6 adjacent to intact skin 8. The wound cavity 6 includes a wound bed 10 prepared for NPWT and transdermal oxygen flow therapy with an exemplary embodiment of a dressing 12 for applying such wound care therapy. The dressing 12 may include a wicking layer 14 which abuts and covers the wound bed. The wicking layer 14 may be made from moisture-wicking synthetic fabric 16 (e.g., Under Armour® or similar fabric). The wicking layer 14 may draw exudates away from the wound and aid in establishing a contiguous flow of oxygen across the wound bed. The wicking layer 14 may include an oxygen delivery manifold 18 to encourage topical delivery of oxygen to the wound. Additionally, the wicking layer 14 may include a mixed gas and exudates removal manifold 20. This manifold may facilitate distributed oxygen flow across the wound bed, and may promote waste gas and exudates removal from the wound. The manifolds may be placed contralaterally within the wound bed to promote oxygen flow distribution and enhance contact time. The oxygen delivery manifold 18 may be connected to a first length of flexible tubing 22. The first length of flexible tubing 22 may include a standardized fluid fitting 24 (e.g., Luer Lock fitting) for connecting the other end of the flexible tubing to the oxygen supply port of a wound care device. Similarly, the waste gas and exudates removal manifold 20 may be connected to a second length of flexible tubing 26. The second length of flexible tubing 26 may include a standardized fluid fitting 24 (e.g., Luer Lock fitting) for connecting the other end of the second length of flexible tubing to an intermediate waste canister or directly to the vacuum supply port of a wound care device. The tubing 22, 26 may be made from a polymeric material suitable for use in hospital applications. Suitable materials for use in the tubing include, but are not limited to, silicone, polyethylene, polypropylene, polyurethane and various other thermoplastics.

The dressing 12 further may include an absorbent layer 28 above the manifold and wicking layer. The absorbent layer 28 may hold exudates that are transported through the wicking layer. The absorbent layer 28 may provide structural support for the wound, the manifold and the first and second lengths of tubing. Additionally, the absorbent layer 28 may provide a protective barrier for the wound bed against physical trauma or microorganisms. In one embodiment, the absorbent layer 28 may be gauze. In another embodiment, the absorbent layer 28 may be polyurethane foam.

The dressing 12 further may include a semi-occlusive layer 30. The semi-occlusive layer 30 may be a sheet of transparent film. The sheet of transparent film may include adhesive on one side to help create an air tight seal around the perimeter of the wound bed. The semi-occlusive layer 30 may include penetrations 32 for passage of the first and second lengths of tubing 22, 26. The penetrations 32 may be located above the dressing manifolds. Sealant may be applied around the penetration and the flexible tubing to form air tight seals. In one embodiment, the sheet of film may be a Tegaderm® dressing manufactured by 3M.

During therapy, the oxygen port on the dressing (i.e., the first length of tubing 22) may be connected via flexible tubing or other conduit to an oxygen source for delivering oxygen to the wound. The vacuum port on the dressing (i.e., the second length of tubing 26) may be connected via flexible tubing or other conduit to a vacuum source for applying negative pressure to the wound. For example, oxygen may be delivered to the wound bed at an average pressure of approximately 760 mmHg; whereas, the applied negative pressure may range from approximately 50 mmHg to approximately 200 mmHg. The net partial pressure of oxygen on the wound surface may be in the range of 560 mmHg to 710 mmHg.

A liquid trap may be disposed between the vacuum source and the tubing which connects the vacuum source to the vacuum port of the dressing. The liquid trap may be located inside or outside of the mechanical pump housing. A liquid trap, however, also may be situated on the discharge side of the mechanical pump. A liquid trap further may include baffles, absorbent material, valves, conduit, and fittings such that the liquid trap contains exudates that are discharged from the wound dressing without leakage independent of the orientation of the device. The liquid trap may operate based on mechanical principles or chemical-mechanical principles.

Figure 2:
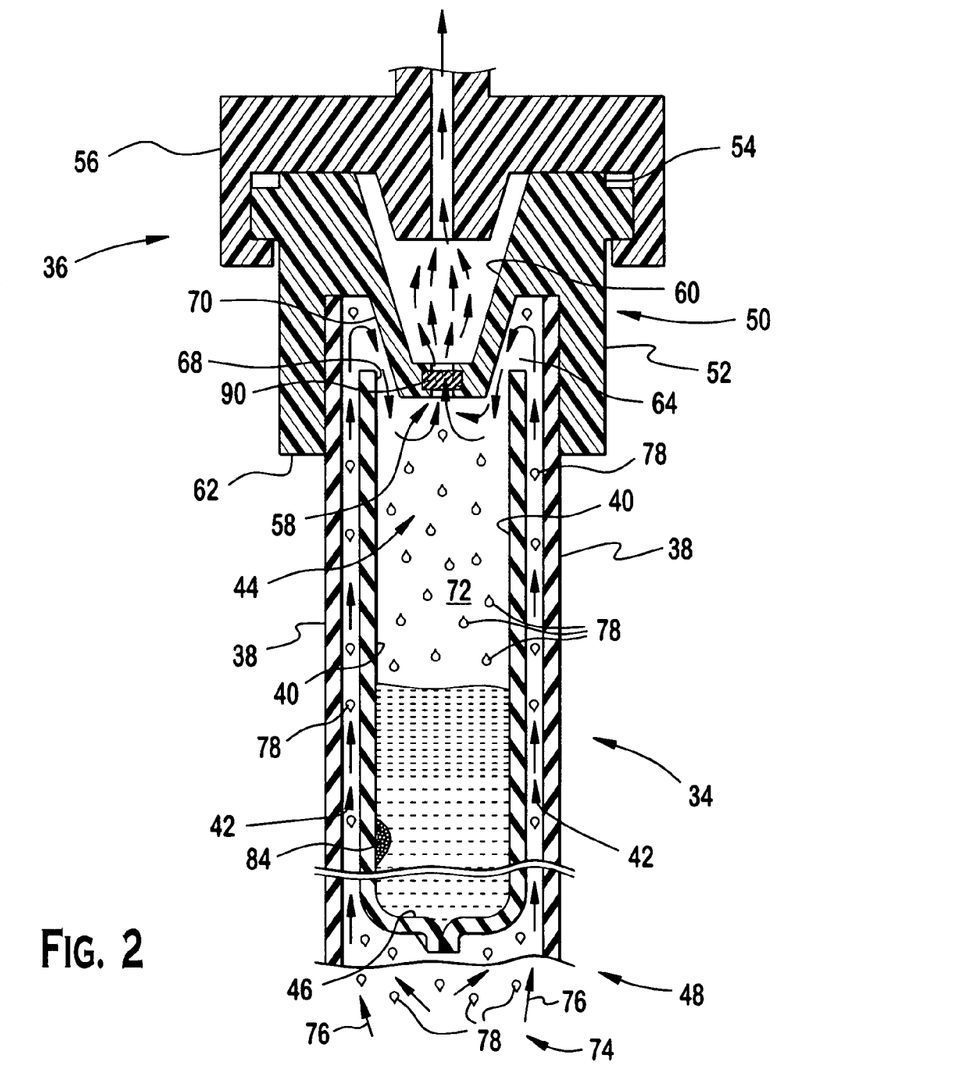
FIG. 2 is a schematic diagram of an exemplary embodiment of a multi lumen tubing and connector system for transporting waste gases and exudate from the dressing assembly of FIG. 1.

The dressing 12 for applying transdermal oxygen therapy and/or negative pressure wound therapy to a wound may use a multi lumen tubing and connector system in addition to or in place of the tubing. FIG. 2 shows a multi lumen tubing 34 and connector system 36 for use in the dressing assembly of FIG. 1.

As shown in FIG. 2, the multi lumen tubing 34 may include a double wall containment structure. A first wall 38 may form an outer wall of the double wall containment structure. A second wall 40 may form a concentric inner wall of the double wall containment structure. The double wall containment structure may define two conduits 42, 44. A first conduit 42 may be bounded by the interior sidewall of the outer wall and the exterior sidewall of the inner wall. The first conduit 42 may have a cross section of annular shape. The second conduit 44 may be bounded by the interior sidewall of the inner wall, and may possess a cross section of circular shape. The second conduit 44 further may include an end wall 46 that seals one end 48 of the second conduit. The opposite end 50 of the multi lumen tubing 34 may be received in a connector body.

Figure 3:
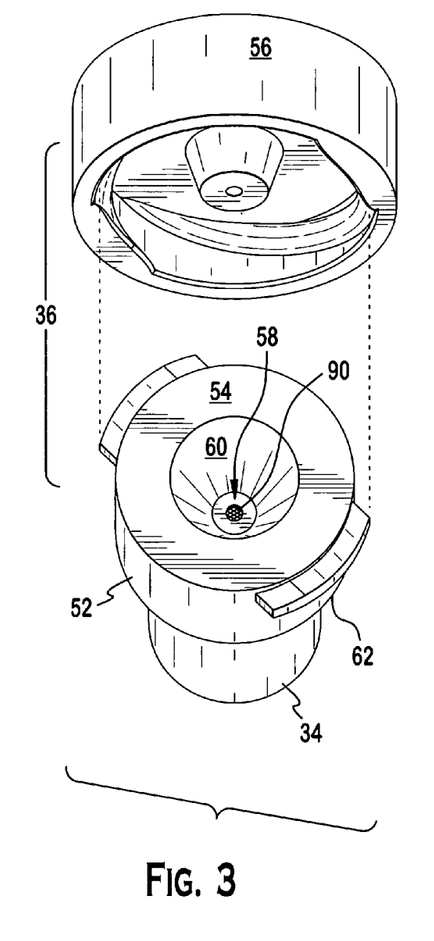
FIG. 3 is an exploded view of the connector system of FIG. 2.
Figure 4:
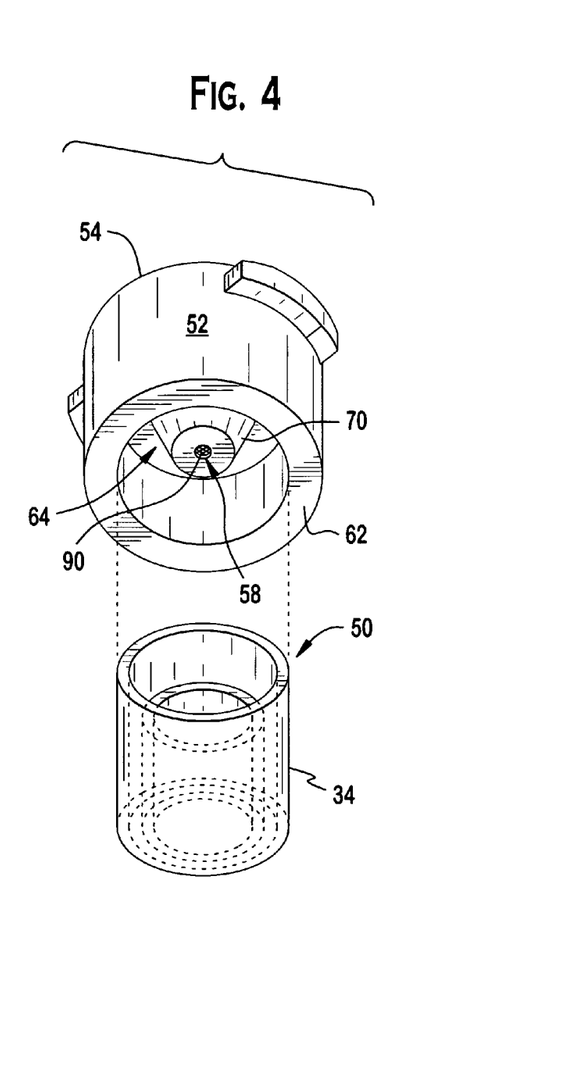
FIG. 4 is an exploded view of a connector body and the multi lumen tubing of FIG. 2.

Referring to FIG. 2, FIG. 3 and FIG. 4, the connector body 52 may include a first end 54 for mechanically connecting to a mating port 56, as well as a second end 62 which may be configured and dimensioned to receive the opposite end 50 of the double wall containment structure. As shown in FIG. 2 and FIG. 3, the connector body 52 may be configured and dimensioned to fluidly connect the opposite end 50 of the double wall containment structure to the mating port 56. The connector body 54 may include a nozzle 60 which docks with the mating port 56 to fluidly connect the multi lumen tubing 34 to the mating port. As shown in FIG. 2 and FIG. 4, the second end 62 of the connector further may include a liquid-gas separator 64. The liquid-gas separator 64 may be integral to the connector body. Alternatively, the liquid gas separator may be formed in conjunction with the multi lumen tubing or in combination with other parts.

Referring to FIG. 2, the liquid-gas separator 64 may connect the annular conduit 42 to the connector body outlet 58 and the inner conduit 44 via one or more passages 68 that include at least one abrupt change in direction. The passage 68 may be configured and dimensioned to separate waste gases and liquids from the annular conduit 42 such that when a waste gas and liquid mixture flows through the one or more passages 68, the direction of flow changes abruptly, and inertia causes liquids to continue in one direction of flow (e.g., downward into the inner conduit), but allows the gas component (which more readily assumes the change of flow direction) to flow in another direction (e.g., toward the connector body outlet) away from the liquid mist particles.

Thus, movement of waste gas liquid mixture 74 within the second end 62 of the connector body 52 may result in separation of liquid mist 78 from the gas component 76 because gases may more readily assume a change of flow direction and will flow away from the liquid mist particles. The liquid mist 78 may coalesce on a surface 70 or fall into a liquid containment area 72 (e.g., inner conduit area). Separation of liquid and gas further may be affected with either a sudden increase or decrease in gas velocity. For instance, with a decrease in velocity, the higher inertia of the liquid mist may carry it forward and away from the gas. The liquid further may coalesce on some surface and gravitate to the liquid section of the separator. By contrast, with an increase in gas velocity, the higher inertia of the liquid generally may cause the gas to move away from the liquid, and the liquid may fall to the liquid section of the separator.

Referring to FIG. 2, FIG. 3 and FIG. 4, the connector body 52 may include a hydrophobic filter 90. The hydrophobic filter 90 may be positioned to intercept the flow of waste gas liquid mixture 74 between the second end 62 and the first end 54 of the connector body. The hydrophobic filter 90 may be a gas permeable and liquid impermeable material. For instance, the hydrophobic filter 90 may be a plug fabricated from fiber or porous materials, such as polyethylene (PE), high-density polyethylene (HDPE) and polypropylene (PP)). For example, POREX Pipette Filter Media manufactured by Porex Technologies, 500 Bohannon Road, Fairburn, Ga. 30213 may be suitable for use as a hydrophobic filter media in the connector body. The hydrophobic filter 90 may be positioned in the outlet 58 and/or the nozzle 60 of the connector body. Indeed, the connector body 52 may be molded around the hydrophobic filter 90. Accordingly, the connector body 52 may be specifically configured to enhance gas-liquid separation.

Referring to FIG. 3, a vacuum source (e.g., a mechanical pump intake) from a wound care device may be connected to the mating port 56 of the connector system 36. As shown in FIG. 2, the first end 54 of the connector may be connected to the mating port 56. The second end 62 of the connector may be connected to the multi lumen tubing 34. The first conduit 42 of the multi lumen tubing 34 may be in fluid communication with a wound or dressing headspace. The second conduit 44 may be closed 46 at the wound end 48 and open at the connector body 52. As suction is applied to the first conduit 42, waste gases and exudates may be drawn into the annular conduit 42. When the flow of waste gas and liquid mixture 74 reaches the connector 52, the flow may be forced to change direction, causing the liquid component 78 of the mixture to fall into the second conduit 44 where it may be collected and stored. The second conduit 44 further may contain absorbent material 84 to help retain the exudate and keep it from being pulled in by the pump. The absorbent material, without limitation, may be a foam structure, a sponge, a chemical material that absorbs liquids, or a combination thereof. For example, the absorbant material may be one or more superabsorbent polymers (SAPs). The cross sectional area of the first conduit 42 (e.g., the annular conduit) may be smaller than the cross sectional area of the second conduit 44 (e.g., the circular conduit). This general configuration may be advantageous because a smaller flow area may affect higher waste gases and exudates flow rates that may promote exudate removal and transport away from the wound. Conversely, a larger cross sectional area of the central conduit 44 may be advantageous because a greater volume for collecting and storing liquid waste may be available and because the larger diameter may affect lower flow rates of waste gases which may prevent the vacuum from removing separated exudate. For example, 40" of conduit with a 3.6 mm inner diameter would provide approximately 10 cc of collection volume.

Figure 5:
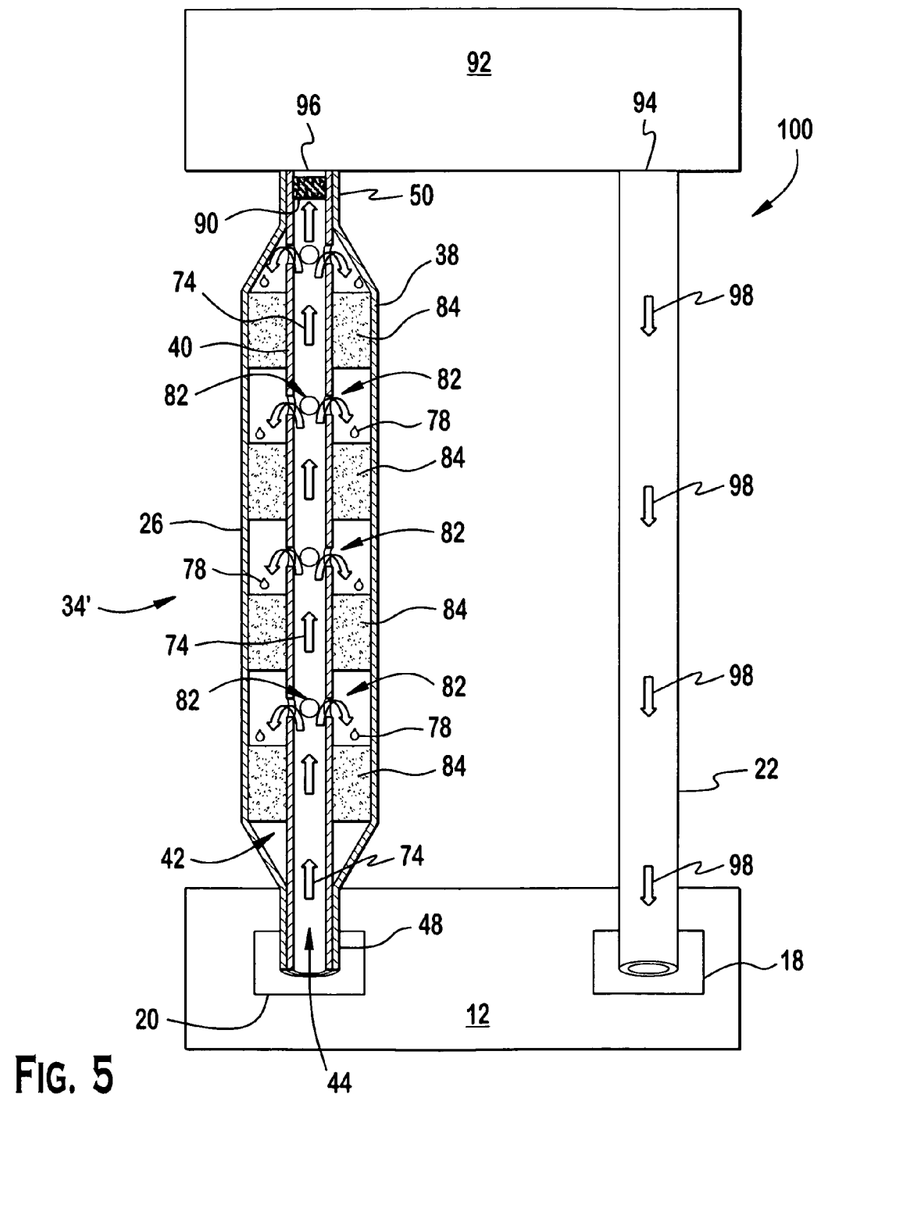
FIG. 5 is a schematic diagram of an exemplary embodiment of a multi lumen tubing and NPWT and topical oxygen delivery (TOD) apparatus for the application of negative pressure wound therapy, transdermal oxygen delivery, or combinations thereof to a wound.

FIG. 5 shows a schematic diagram of another multi lumen tubing 34' and NPWT and topical oxygen delivery (TOD) apparatus 100 for the application of negative pressure wound therapy, transdermal oxygen delivery, or combinations thereof to a wound. The apparatus 100 may include a wound care device 92 that includes an oxygen supply port 94 and a vaccum supply port 96. The apparatus 100 further may include a dressing 12. The oxygen delivery manifold 18 of the dressing 12 may be connected to the oxygen supply port 94 by a first length of tubing 22. The wound exudates removal manifold 20 of the dressing 12 may be connected to the vacuum supply port 96 by a multi lumen tubing 34'.

Figure 6:
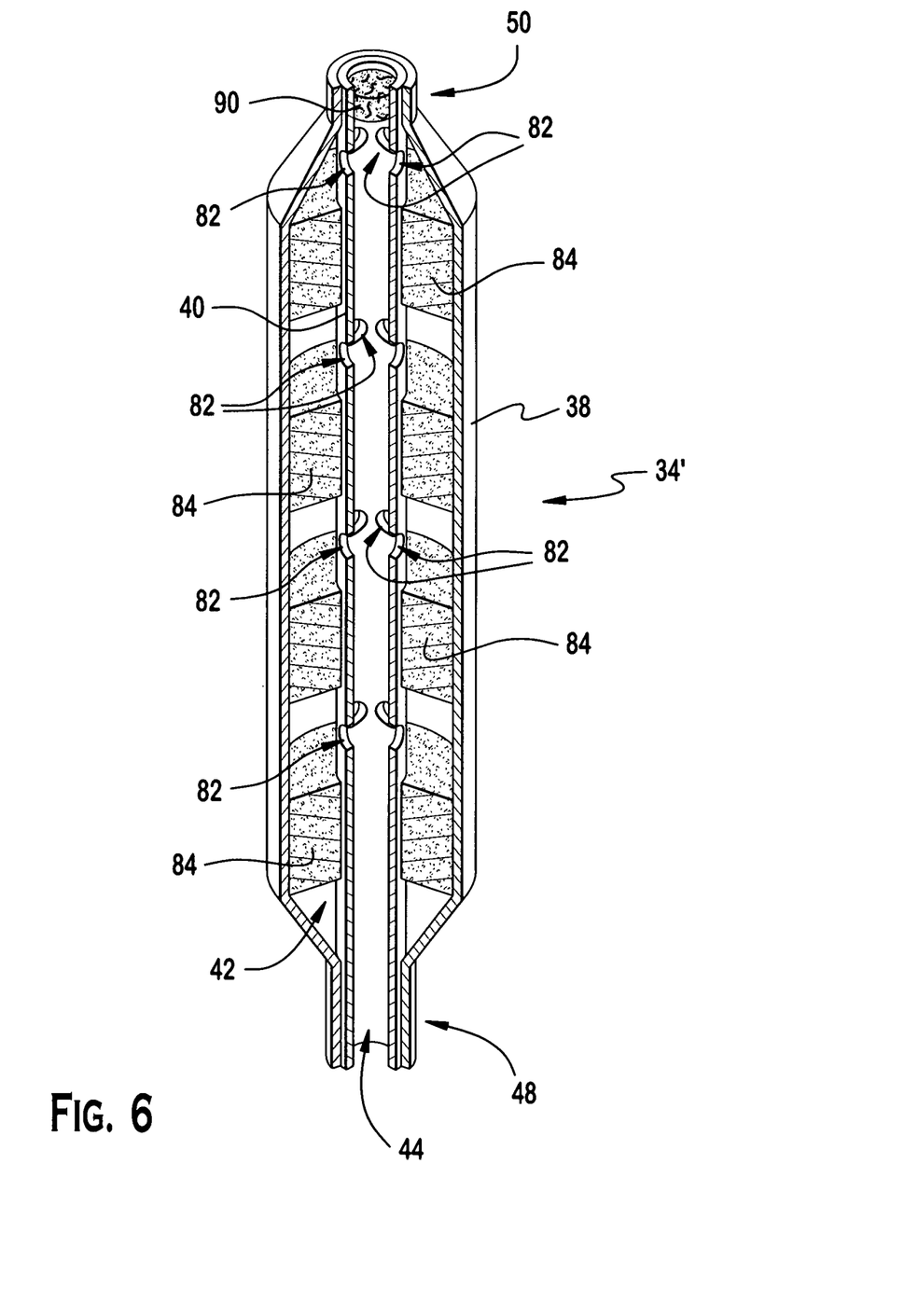
FIG. 6 is a schematic diagram of the multi lumen tubing of FIG. 5.

Referring to FIG. 5 and FIG. 6, the first wall 38 of the multi lumen tubing 34' may be liquid and gas impermeable, but the second wall 40 may be porous. For example, the second wall 40 may be formed from a generally liquid impermeable and gas permeable material but may include openings 82 which fluidly connect the second conduit 44 and the first conduit 42. An absorbent material 84 may be placed in or on the first conduit 42. The absorbent material 84 may be similar to the absorbent materials used in diapers. A hydrophobic filter 90 may be positioned at the discharge end 50 of the multi lumen tubing 34' to prevent liquid from directly exiting the multi lumen tubing. In use, waste gas liquid mixture 74 may flow through the openings 82 and contact absorbent material 84 in the first conduit. The absorbent material(s) 84 may remove liquid 78 from the waste gas liquid mixture flow 74. To promote phase separation and contact of the waste gas liquid mixture with the absorbent materials in the first conduit, an insert 86 may be placed in the second conduit 44 to intercept or disrupt waste gas liquid mixture flow 74.

Figure 7:
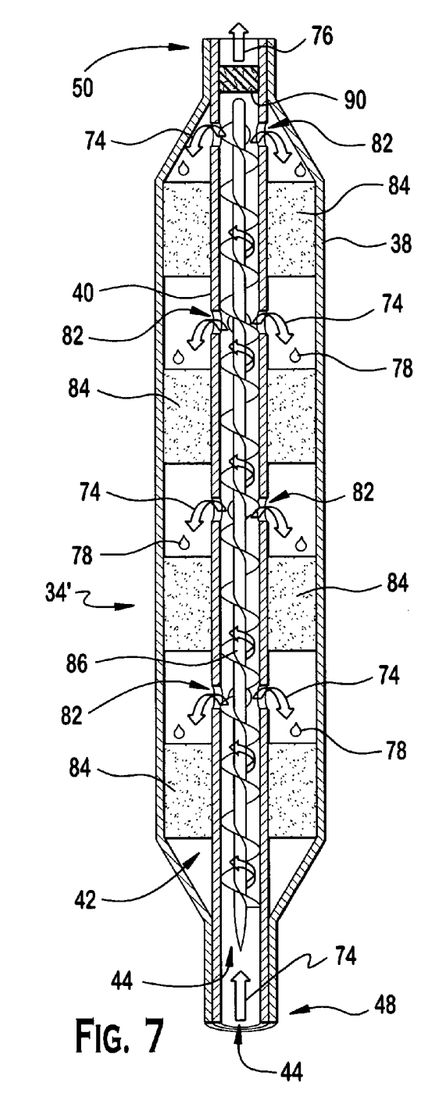
FIG. 7 is a schematic diagram of the multi lumen tubing of FIG. 5 with a turbulence inducing structure.
Figure 8:
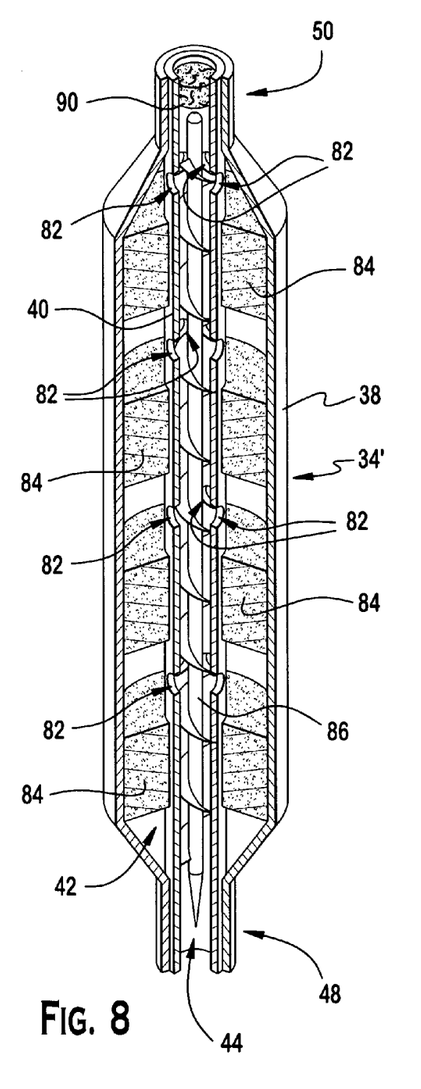
FIG. 8 is a schematic diagram of the multi lumen tubing and insert of FIG. 7.

Referring to FIG. 7 and FIG. 8, a structure or insert 86 may be positioned in the second conduit 44 such that the insert 86 changes the flow path of waste gas liquid mixture 74 and directs the liquid waste 78 toward absorbent material 84 in the first conduit 42. In one example, the insert 86 may include a spiral insert or segment. In use, turbulence, such as vortices may be produced by the interaction of the waste gas liquid flow and insert may enhance phase separation. The presence of a hydrophobic filter 90 further may enhance phase separation and prevent liquid waste from leaving the multi lumen tubing. The structure or insert 86 may be integrally formed as part of the second conduit 44. Accordingly, a turbulence inducing structure(s), such as a spiral shape and/or an arrangement of one or more baffles may be molded in as part of the inner wall of the second conduit. For example, without limitation, a turbulence inducing structure may be coextruded with the second conduit or the second conduit may be molded over the turbulence inducing structure.

The foregoing devices for the collection, transport and containment of exudate wastes from wound care may be used with a wound care device and a wound dressing assembly to provide negative pressure wound therapy, transdermal oxygen therapy, or combinations thereof to a wound. These consumables may be replaced on an as needed basis. Thus, the dressing 12, tubing 22, 26, multi lumen tubing(s) 34, 34', and connector body 52 described herein may be available in individually sealed sterile packaging.

While it has been illustrated and described what at present are considered to be embodiments of the present invention, it will be understood by those skilled in the art that various changes and modifications may be made, and equivalents may be substituted for elements thereof without departing from the true scope of the invention. For example, in some clinical applications it may be efficacious to place one or more segments of a multi lumen tubing between the second length of tubing and a third length of tubing connected to a vacuum source of a wound care device. Similarly, it may be to useful to place one or more segments of a multi lumen tubing between the first length of tubing and a fourth length of tubing connected to a therapeutic gas supply (e.g., oxygen) of a wound care device. Additionally, features and/or elements from any embodiment may be used singly or in combination with other embodiments. Therefore, it is intended that this invention not be limited to the particular embodiments disclosed herein, but that it have the full scope defined by the language of the following claims, and equivalents thereof.

What is claimed is:

1. A device for transporting waste gases and liquid exudates from a wound comprising:
    a multi lumen tubing comprising,
        a double wall containment structure which comprises
            a first wall which forms an outer containment structure for a first lumen, the outer containment structure including
                a first end portion,
                a second end portion, and
                a first longitudinal axis extending from the first end portion to the second end portion, and
            a second wall which forms a tube that defines a second lumen, the tube being spaced from the first wall such that the first and second walls are concentrically aligned about the first longitudinal axis, and such that the first wall and the second wall define the first lumen;
    a connector for securing the multi lumen tubing to a fitting, the connector comprising
        a body having a second longitudinal axis such that the body comprises
            a first end surface which comprises a first cavity extending into the body from the first end surface, the first cavity being bounded radially about the second longitudinal axis by a first cavity side wall,
            a second end surface spaced from the first end surface along the second longitudinal axis, the second end surface comprises
                a second cavity extending into the body from the second end surface, the second cavity being bounded radially about the second longitudinal axis by a second cavity side wall, an interior wall located between the first cavity and the second cavity, the interior wall forming a projection in the second cavity, the projection comprising
                    an outer surface facing the second cavity side wall, and
                    a ledge adjacent the outer surface, the ledge comprising a bore extending between the first cavity and the second cavity, and
                    a hydrophobic filter positioned in the bore such that the hydrophobic filter forms a gas permeable and a liquid impermeable barrier between the second cavity and the first cavity.

2. The device of claim 1, wherein the second cavity and the second cavity side wall are configured and dimensioned to connect the multi lumen tubing to the connector.

3. The device of claim 2, wherein the second cavity and the second cavity side wall are configured and dimensioned to telescopically receive the first wall of the outer containment structure.

4. The device of claim 3, wherein the outer surface of the projection, the first wall of the double wall containment structure, and the second wall of the double wall containment structure cooperate to form a passage that fluidly connects the first lumen, the second lumen and the bore extending between the first cavity and the second cavity.

5. The device of claim 4, wherein the passage that fluidly connects the first lumen, the second lumen, and the bore extending between the first cavity and the second cavity is configured and dimensioned to form a liquid-gas separator such that a liquid-gas mixture being conveyed from the first lumen to the second lumen changes flow direction abruptly to separate liquid from the liquid-gas mixture.

6. The device of claim 5, wherein the ledge extends into the second lumen.

7. The device of claim 1, wherein the second lumen comprises a blind end.

8. The device of claim 1, wherein the second lumen houses absorbent material.

9. The device of claim 8, wherein the absorbent material comprises one or more superabsorbent polymers.

10. The device of claim 1, wherein the multi lumen tubing is flexible.

11. The device of claim 10, wherein the multi lumen tubing is designed to convey gases under negative pressure.

12. The device of claim 11, wherein the multi lumen tubing is designed to convey a waste gas liquid mixture from a wound.

13. The device of claim 1, wherein the first lumen has a first cross-section perpendicular to the first longitudinal axis, the first cross-section having annular shape.

14. The device of claim 13, wherein the second lumen has a second cross-section perpendicular to the first longitudinal axis, the second cross-section being of different shape than the first cross-section.

15. The device of claim 14, wherein the second cross-section has circular shape.

16. The device of claim 1, wherein the hydrophobic filter comprises a plug of filter media.

17. The device of claim 16, wherein the filter media is a POREX filter media.

18. The device of claim 1, wherein the body is configured and dimensioned to mate with a standardized fluid fitting.

* * * * *